(12) United States Patent
Franz et al.

(10) Patent No.: US 11,666,247 B2
(45) Date of Patent: Jun. 6, 2023

(54) METHOD, DEVICE AND COMPUTER PROGRAM FOR CAPTURING OPTICAL IMAGE DATA OF PATIENT SURROUNDINGS AND FOR IDENTIFYING A PATIENT CHECK-UP

(71) Applicant: Drägerwerk AG & Co. KGaA, Lübeck (DE)

(72) Inventors: Frank Franz, Stockelsdorf (DE); Stefan Schlichting, Lübeck (DE); Jasper Diesel, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 439 days.

(21) Appl. No.: 16/630,284

(22) PCT Filed: Jul. 5, 2018

(86) PCT No.: PCT/EP2018/068204
§ 371 (c)(1),
(2) Date: Jan. 10, 2020

(87) PCT Pub. No.: WO2019/011769
PCT Pub. Date: Jan. 17, 2019

(65) Prior Publication Data
US 2020/0196913 A1    Jun. 25, 2020

(30) Foreign Application Priority Data

Jul. 11, 2017   (DE) .................. 102017006529.2

(51) Int. Cl.
*G06K 9/00*    (2022.01)
*A61B 5/11*    (2006.01)
(Continued)

(52) U.S. Cl.
CPC .......... *A61B 5/1113* (2013.01); *A61B 5/1121* (2013.01); *A61B 5/1128* (2013.01);
(Continued)

(58) Field of Classification Search
CPC .................................................. A61B 5/1113
See application file for complete search history.

(56) References Cited

U.S. PATENT DOCUMENTS 10,475,206 B1 * 11/2019 Rush ..................... G06T 7/254
2012/0075464 A1   3/2012 Derenne et al.
(Continued)

FOREIGN PATENT DOCUMENTS

DE     102015013031 A1    4/2017
JP     H11149465 A        6/1999
(Continued)

OTHER PUBLICATIONS

Jorch, G., Kluge, S., König, F., Markewitz, A., Notz, K., Parvu, V., . . . , Waydhas, C. (2010), Recommendations for the Structure and Outfitting of Intensive Care Units, Adopted by Decision of the Presidium of the German Interdisciplinary Association of Intensive Care and Emergency Medicine (DM).
Goran, S. (Aug. 2010), A Second Set of Eyes: An Introduction to Tele-ICU, Critical-CareNurse.
Ahad, M. A., Tan, J. K., Kim, H., and Ishikawa, S. (2012), Motion history image: its variants and applications, Machine Vision and Applications.
(Continued)

*Primary Examiner* — Oneal R Mistry
(74) *Attorney, Agent, or Firm* — McGlew and Tuttle, P.C.

(57) ABSTRACT

A method, an apparatus and a computer program for capturing optical image data of patient surroundings and for identifying a patient check-up. The method (10) for capturing optical image data of patient surroundings and for identifying a patient check-up on the basis of the image data includes detecting (12) the patient on the basis of the image data. There is a detecting (14) of at least one further person on the basis of the image data and determining (16) at least one geometric relation between the patient and the at least
(Continued)

one further person. The determining (16) of the geometric relation includes determining an orientation or a viewing direction of the at least one further person in relation to the patient. The method further includes identifying (18) the patient check-up on the basis of the geometric relation.

21 Claims, 10 Drawing Sheets

(51) Int. Cl.
    *G06T 7/70*     (2017.01)
    *G16H 40/67*     (2018.01)
    *G16H 40/20*     (2018.01)
    *G06T 7/60*     (2017.01)
    *G08B 21/02*     (2006.01)

(52) U.S. Cl.
    CPC ............... *G06T 7/60* (2013.01); *G06T 7/70* (2017.01); *G08B 21/02* (2013.01); *G16H 40/20* (2018.01); *G16H 40/67* (2018.01); *G06T 2207/30196* (2013.01)

(56) References Cited

U.S. PATENT DOCUMENTS

| | | | |
|---|---|---|---|
| 2012/0154582 A1 | 6/2012 | Johnson et al. | |
| 2014/0005502 A1* | 1/2014 | Klap | A61B 5/1116 600/300 |
| 2014/0093135 A1 | 4/2014 | Reid et al. | |
| 2014/0270363 A1 | 9/2014 | Chakraborty et al. | |
| 2014/0270482 A1 | 9/2014 | Chakraborty et al. | |
| 2015/0261924 A1* | 9/2015 | Geleijnse | A61B 5/7246 705/2 |
| 2015/0262338 A1* | 9/2015 | Xu | G06T 7/20 382/128 |
| 2015/0281659 A1* | 10/2015 | Hood | H04N 7/188 348/143 |
| 2016/0183864 A1 | 6/2016 | Kusens et al. | |
| 2017/0155877 A1* | 6/2017 | Johnson | G06V 20/52 |
| 2018/0192923 A1* | 7/2018 | Fu | A61B 5/1115 |

FOREIGN PATENT DOCUMENTS

| | | |
|---|---|---|
| JP | 2008276552 A | 11/2008 |
| JP | 2012519547 A | 8/2012 |
| WO | 2015055312 A1 | 4/2015 |
| WO | 2016071314 A1 | 5/2016 |
| WO | 2016135069 A1 | 9/2016 |

OTHER PUBLICATIONS

Barnich, O., Van Droogenbroeck, M. (2011), ViBe: A universal background subtraction algorithm for video sequences, Image Processing, IEEE Transactions on.
Breiman, L. (2001), Random Forests, Machine Learning, pp. 5-32.
Dalal, N., Triggs, B. (2005), Histograms of Oriented Gradients for Human Detection, IEEE Computer Society Conference on Computer Vision and Pattern Recognition.
Fanelli, G., Weise, T., Gall, J., St Van Gool, L. (2011), Real time head pose estimation from consumer depth cameras, Pattern Recognition.
Fischler, M. A. (1981), Random sample consensus: a paradigm for model fitting with applications to image analysis and automated cartography, Communications of the ACM, pp. 381-395.
Girardeau-Montaut, D., et al., e. (2005), Change detection on points cloud data acquired with a ground laser scanner, International Archives of Photogrammetry, Remote Sensing and Spatial Information Sciences.
Hartman, F. (2011), Robot control by gestures.
Krizhevsky, A., Sutskever, I., and Hinton, G. E. (2012), Imagenet classification with deep convolutional neural networks, Advances in neural information processing systems, pp. 1097-1105.
Lallemand, J., Ronge, A., Szczot, M., Ilic, S. (2014), Pedestrian orientation estimation, pp. 476-487, Springer.
Martinez, M., Schauerte, B., Stiefelhagen, R., 2013, "BAM!" Depth-Based Body Analysis in Critical Care, International Conference on Computer Analysis of Images and Patterns, pp. 465-472.
Rehder, E., Kloeden, H., Stiller, C., 2014, Head detection and orientation estimation for pedestrian safety, 17th International IEEE Conference on Intelligent Transportation Systems (ITSC), pp. 2292-2297.
Song, S., Xiao, J. (2014), Sliding shapes for 3D object detection in depth images, European Conference on Computer Vision, pp. 634-651.
Welch, G., Bishop, G. (Jul. 2006), An Introduction to the Kalman Filter.
Alessandra Guimarães et al. "Proxemic behavior of nursing in the hemodialysis setting Comportamento proxêmico da enfermagem no espaço da hemodiálise" Acta Paulista De Enfermagem, vol. 30, No. 04, Aug. 7, 2017 (Aug. 7, 2017), pp. 343-349.
Alonso Patron-Perez: Structured Learning of Human Interactions in TV Shows. IEEE Transactions on Pattern Analysis and Machine Intelligence, Jan. 17, 2012, vol. 34, No. 12, 2441-2453.
Jos Wind, "Human Interaction Recognition from Video", Master Thesis, Department of Information and Computing Sciences, Utrecht University, Mar. 2017.

* cited by examiner

METHOD, DEVICE AND COMPUTER PROGRAM FOR CAPTURING OPTICAL IMAGE DATA OF PATIENT SURROUNDINGS AND FOR IDENTIFYING A PATIENT CHECK-UP

CROSS REFERENCE TO RELATED APPLICATIONS

This application is a United States National Phase Application of International Application PCT/EP2018/068204, filed Jul. 5, 2018, and claims the benefit of priority under 35 U.S.C. § 119 of German Application 10 2017 006 529.2, filed Jul. 11, 2017, the entire contents of which are incorporated herein by reference.

TECHNICAL FIELD

Exemplary embodiments pertain to a method, to a device and to a computer program for capturing optical image data of patient surroundings and for identifying a patient checkup, especially but not exclusively to a concept for the automated identification of patient checkups by nursing staff, based on which an automated documentation or even alarm generation can be established.

TECHNICAL BACKGROUND

An automatic monitoring of patients in intensive care units is carried out in the conventional technique primarily by monitoring vital parameters by medical devices (e.g., hemodynamic monitoring, ventilator) at bedside. The medical devices shall generate an alarm when undesired physiological states develop. It is, however, just as important to monitor state variables such as the activity of the patient or the identification of dangerous situations such as falls.

Such monitoring has hitherto been carried out mainly by attending nursing staff who should look after the patient at times at very close intervals, depending on the patient's state, which in turn is associated with enormous costs. On the other hand, any manipulation at/of the patient may be associated with stress, so that the patient will not sometimes have phases of rest of a sufficient duration.

According to the German Interdisciplinary Association for Intensive Care and Emergency Medicine [Deutsche Interdisziplinäre Vereinigung für Intensiv-und Notfallmedizin], the nursing care ratio of patients to nursing staff in intensive care units should be 2:1 at most (cf. Jorch et al., 2010), but it is often markedly higher in reality. Especially as a result of this, the patient may be unattended for excessively long time periods and monitoring of the corresponding time intervals is advisable. On the other hand, it is possible that a patient will not have sufficient phases of rest because he is disturbed by actions taken by the medical staff all too often. The absence of a normal circadian rhythm, which demonstrably has an adverse effect on the healing process, is associated with this, among other things. Monitoring and a limitation of the duration of the manipulations of the patient may consequently be meaningful here.

Many different approaches to the problem of the high manpower demand for monitoring the patient have already been taken. By contrast, it is hardly possible nowadays to monitor, in particular, patient check-ups and manipulations. Some procedures and systems will be discussed below.

Patient monitoring is the monitoring of vital parameters by medical devices (hemodynamic monitoring, ventilator) at bedside and is the standard in the automatic monitoring of patients in intensive care units. The medical devices are able to generate an alarm for the medical staff when a vital parameter being monitored is outside a certain range. They thus relieve the staff and make possible the monitoring of certain parameters. Medical devices are not able at present to fully replace the nursing staff and have hardly any context information, i.e., they are very patient-fixed and they are therefore also unable to detect and hence monitor the checking and manipulation of a patient.

Tele-ICUs (from English Intensive Care Unit) have played a role since about 2000, especially in the USA. Video and audio data are transmitted together with measured vital parameters to a remotely located station. Staff, which analyzes the data, is located there (review: (Goran, 2010)). Tele-ICUs thus contribute to reducing the manpower costs, since a staff member can observe a plurality of display screens simultaneously more easily than a plurality of bedsides. A personal contact with the patient is important and necessary, e.g., in order to reposition the patient, with Tele-ICU systems as well, and even though the time intervals of these contacts could be checked with Tele-ICU systems, this leads to an increase in the burden for the staff members in the Tele-ICU station.

The shifts for the individual nursing staff members are, of course, scheduled in an intensive care unit. This comprises at least the time and the location (usually including the assigned bedsides). The scheduling does not, as a rule, necessarily ensure that the time intervals for the checkings are, in fact, also observed, and it is not necessarily an accurate picture of reality.

There are currently no camera-based monitoring systems for the intensive care unit, in which algorithms automatically identify defined events. US 2016 183 864 A1 describes a method, which measures the time during which a person is located in a defined zone around the patient and compares this measured time with a set time. Data of a depth camera are used as input data. However, the fact that a person is located in a virtual zone around the patient does not yet mean that this person checks or even manipulates the patient.

Additional information is found in:
US 2016 183 864 A1,
Ahad, M. A., Tan, J. K., Kim, H., and Ishikawa, S. (2012), Motion history image: its variants and applications, Machine Vision and Applications,
Barnich, O., Van Droogenbroeck, M. (2011), ViBe: A universal background subtraction algorithm for video sequences, Image Processing, IEEE Transactions on,
Breiman, L. (2001), Random Forests, Machine Learning, pp. 5-32,
Dalal, N., Triggs, B. (2005), Histograms of Oriented Gradients for Human Detection, IEEE Computer Society Conference on Computer Vision and Pattern Recognition,
Fanelli, G., Weise, T., Gall, J., St Van Gool, L. (2011), Real time head pose estimation from consumer depth cameras, Pattern Recognition,
Fischler, M. A. (1981), Random sample consensus: a paradigm for model fitting with applications to image analysis and automated cartography, Communications of the ACM, pp. 381-395,
Girardeau-Montaut, D., et al., e. (2005), Change detection on points cloud data acquired with a ground laser scanner, International Archives of Photogrammetry, Remote Sensing and Spatial Information Sciences,
Goran, S. (August 2010), A Second Set of Eyes: An Introduction to Tele-ICU, Critical-CareNurse,
Hartman, F. (2011), Robot control by gestures, Jorch, G., Kluge, S., Konig, F., Markewitz, A., Notz, K., Parvu, V., . . . , Waydhas, C. (2010), Recommendations for the Structure and Outfitting of Intensive Care Units, Adopted by Decision of the Presidium of the German Interdisciplinary Association of Intensive Care and Emergency Medicine (DIVI), Krizhevsky, A., Sutskever, I., and Hinton, G. E. (2012), Imagenet classification with deep convolutional neural networks, Advances in neural information processing systems, pp. 1097-1105, Lallemand, J., Ronge, A., Szczot, M., Ilic, S. (2014), Pedestrian orientation estimation, pp. 476-487, Springer, Martinez, M., Schauerte, B., Stiefelhagen, R., 2013, "BAM!" Depth-Based Body Analysis in Critical Care, International Conference on Computer Analysis of Images and Patterns, pp. 465-472, Rehder, E., Kloeden, H., Stiller, C., 2014, Head detection and orientation estimation for pedestrian safety, 17th International IEEE Conference on Intelligent Transportation Systems (ITSC), pp. 2292-2297, Song, S., Xiao, J. (2014), Sliding shapes for 3D object detection in depth images, European Conference on Computer Vision, pp. 634-651, and Welch, G., Bishop, G. (July 2006), An Introduction to the Kalman Filter.

SUMMARY

Therefore, there is a need for providing an improved concept for identifying patient check-ups. This need is met by exemplary embodiments of a method, of a device and of a computer program according to the invention.

Some exemplary embodiments can identify patient check-ups or patient manipulations, for example, automatically and reliably on the basis of image data. It can thus be better ensured in at least some exemplary embodiments that the check-ups and manipulations take place at adequate time intervals in order to guarantee an appropriate medical care and nursing with sufficient phases of rest. A check-up is defined mainly as a visual checking of the patient, e.g., when a nursing staff member is looking at the patient over a certain time or is oriented towards the patient. A manipulation of the patient implies a physical contact. Some exemplary embodiments can assume precisely this check-up automatically, reliably and in a trouble-free manner. As a result, the care for the patient can improve and the costs can possibly be reduced by better planning.

Exemplary embodiments are based on the basic idea that information on a geometric relation between the nursing staff member and the patient can be determined within the framework of an orientation or a viewing direction of the nursing staff member from image data of patient surroundings in which a nursing staff member is located. It can be determined based on this information whether a patient check-up or a patient manipulation has taken place. The reliability of the determination via the geometric relation is improved compared to a mere determination of whether the patient and the nursing staff member are located in the same room or capture area.

Exemplary embodiments provide a method for capturing optical image data of patient surroundings and for identifying a patient check-up based on the image data. The method comprises a detection of the patient based on the image data and a detection of at least one additional person based on the image data. The method further comprises a determination of at least one geometric relation between the patient and the at least one additional person. The method comprises, moreover, an identification of the patient check-up based on the geometric relation, the determination of the geometric relation comprising a determination of an orientation and/or of a viewing direction of the at least one additional person in relation to the patient. Exemplary embodiments can reliably identify patient check-ups by determining the orientation or the viewing direction of the at least one additional person.

In some additional exemplary embodiments, the determination of the geometric relation may comprise a determination of a distance between the at least one additional person and the patient. Exemplary embodiments can thus possibly also identify a patient manipulation. The determination of the geometric relation may comprise in some exemplary embodiments an identification of a contact between the at least one additional person and the patient and thus reliably detect a patient check-up or a manipulation of the patient. In additional exemplary embodiments, the method may comprise an outputting of information on a time period, during which the geometric relation between the patient and the at least one additional person was present. The identification of a patient check-up may therefore be linked to a duration of the presence of the geometric relation and thus be made even more reliable. Moreover, at least some exemplary embodiments may carry out a checking of a time interval for the patient check-up and an outputting of a warning when identified patient check-ups deviate from the time interval. An automated monitoring or a warning mechanism can thus be made possible. For example, the checking of the time interval may comprise an analysis of a time of day-dependent function together with one or more weighted geometric relations, so that a plurality of relevant parameters can be included in the mechanism.

An identification of whether the at least one additional person is a nursing staff member and, moreover, an identification of the patient check-up can take place in some exemplary embodiments on the basis of the at least one geometric relation when the person is a nursing staff member. Misidentifications or incorrect detections of patient check-ups can thus be reduced. The identification of whether the at least one additional person is a nursing staff member can be based, for example, an a color analysis of pixels of the at least one additional person in the image data, e.g., a clothing color can be detected. The identification of the nursing staff member may be based, in general, on an identifier of the staff member, for which different mechanisms are conceivable. Examples are optical identifiers, acoustic identifiers, but also electronic identifiers, etc.

Determination of a plurality of additional persons in the patient's surroundings may be carried out in some exemplary embodiments. It is thus possible, for example, to distinguish physicians, nursing staff and visitors. The method may be carried out in some exemplary embodiments after receiving alarm information from a medical device. Exemplary embodiments may thus carry out the method due to triggering by an alarm (for example, by a critical vital parameter) and determine, for example, a time between alarm generation and a performed patient check-up. The method can also monitor in further exemplary embodiments whether a patient check-up takes place within a predefined time period after receipt of the alarm information. Exemplary embodiments may thus possibly facilitate a documentation by a timer function being taken into consideration and it being documented whether a patient check-up takes place within a time monitored by the timer function. A determination of information on whether the patient should be checked more frequently or less frequently and an outputting of this information may be carried out in further exemplary embodiments. Exemplary embodiments can thus make possible a warning system and/or an automated monitoring. For example, a documentation of identified patient check-ups may then also be carried out in an automated manner or facilitated.

Exemplary embodiments also provide a device with a computer, which is configured to execute a method in accordance with one of the above claims.

Another exemplary embodiment is a program or computer program with a program code for executing a method described here when the program code is executed on a computer, on a processor or on a programmable hardware component.

Further advantageous embodiments will be described in more detail below on the basis of the exemplary embodiments shown in the drawings, to which exemplary embodiments are generally but not entirely limited.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
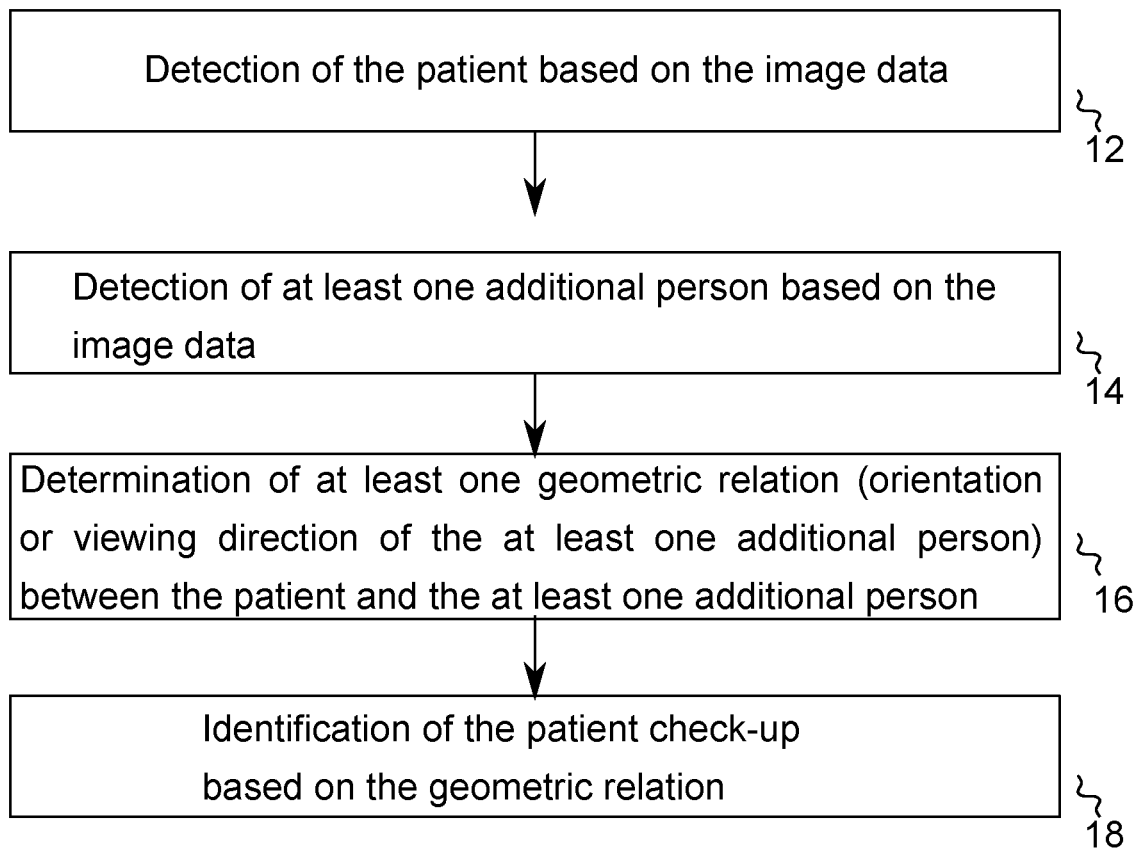
FIG. 1 is a block diagram of an exemplary embodiment of a method for capturing optical image data of patient surroundings and for identifying a patient check-up based on the image data.

Referring to the drawings, different exemplary embodiments will now be described in more detail with reference to the attached drawings, in which some exemplary embodiments are shown.

In the following description of the attached figures, which show only some examples of exemplary embodiments, identical reference numbers may designate identical or comparable components. Further, summary reference numbers may be used for components and objects that occur as multiple components or objects in an exemplary embodiment or in a drawing, but are described together concerning one or more features. Components or objects that are described with identical or summary reference numbers may have an identical configuration but possibly also different configurations concerning individual features, a plurality of features or all features, for example, their dimensions, unless something else explicitly or implicitly appears from the description. Optional components are represented by broken lines or arrows in the figures.

Even though exemplary embodiments may be modified and changed in different manners, exemplary embodiments are shown in the figures as examples and will be described herein in detail. It should, however, be made clear that it is not intended to limit exemplary embodiments to the particular forms disclosed, but exemplary embodiments shall rather cover all functional and/or structural modifications, equivalents and alternatives, which are within the scope of the present invention. Identical reference numbers designate identical or similar components in the entire description of the figures.

It should be noted that an element that is described as being "connected" or "coupled" with another element may be connected or coupled directly with the other element or that elements located in between may be present. If, by contrast, an element is described as being "directly connected" or "directly coupled" with another element, no elements located in between are present. Other terms that are used to describe the relationship between elements should be interpreted in a similar manner (e.g., "between" versus "directly in between," "adjoining" versus "directly adjoining," etc.).

The terminology that is being used here is used only to describe certain exemplary embodiments and shall not limit the exemplary embodiments. As being used herein, the singular forms "a," "an" and "the" shall also include the plural forms, unless something else unambiguously appears from the context. It should further be made clear that the terms such as, for example, "contains," "containing," "has," "comprises," "comprising" and/or "having," as being used herein, indicate the presence of said features, integers, steps, work processes, elements and/or components, but they do not rule out the presence or the addition of one or more features, integers, steps, work processes, elements, components and/or groups thereof.

Unless defined otherwise, all the terms being used herein (including technical and scientific terms) have the same meaning that a person having ordinary skill in the art in the field to which the exemplary embodiment belongs attributes to them. It should further be made clear that terms, e.g., those that are defined in generally used dictionaries, are to be interpreted as if they had the meaning that is consistent with their meaning in the context of the pertinent technique, rather than in an idealized or excessively formal sense, unless this is expressly defined here.

FIG. 1 shows in a block diagram an exemplary embodiment of a method 10 for capturing optical image data of patient surroundings and for identifying a patient check-up based on the image data. The method comprises a detection 12 of the patient based on the image data and a detection 14 of at least one additional person based on the image data. The method 10 comprises, moreover, a determination 16 of at least one geometric relation between the patient and the at least one additional person. The determination 16 of the geometric relation comprises a determination of an orientation or a viewing direction of the at least one additional person in relation to the patient. The method 10 comprises an identification 18 of the patient check-up based on the geometric relation.

Exemplary embodiments also provide a device with a computer, which is configured to execute one of the methods 10 being described here. The computer may correspond in exemplary embodiments to any desired controller or processor or a programmable hardware component. For example, the method 10 may also be embodied as software that is programmed for a corresponding hardware component. The computer may thus be implemented as a programmable hardware with correspondingly adapted software. Any desired processors, such as digital signal processors (DSPs) or graphics processors may be used. Exemplary embodiments are not limited here to a particular type of processor. Any desired processors or even a plurality of processors are conceivable for implementing the computer.

Another exemplary embodiment is a program or computer program with a program code for executing a method being described here when the program code is executed on a computer, on a processor or on a programmable hardware component.

The computer may be coupled in exemplary embodiments with a capturing device, which is adapted to or configured for the capturing of the image data. For example, one or more sensors may be used for capturing the image data. For example, the one sensor or the plurality of sensors of the capturing device capture in such an exemplary embodiment at least three-dimensional (partial) image data and make these available to the computer, which detects or identifies the patient and the at least one additional person in the image data.

The capturing device may be coupled with a determination device and/or with an interface. The capturing device may correspond here to any one or more optical capturing units, capturing devices, capturing modules, sensors, etc. Cameras, image sensors, infrared sensors, sensors for capturing one-, two-, three- or more than three-dimensional data, sensor elements of various types, etc., are conceivable here. The one or more sensors may comprise in other exemplary embodiments at least one sensor, which delivers at least three-dimensional data. The three-dimensional data accordingly capture information on pixels in space and additionally comprise, quasi as additional dimensions, additional information, for example, color information (e.g., red, green, blue (RGB) color space), infrared intensity, transparency information (e.g., alpha values), etc.

There are various types of sensors, which, though not generating a two-dimensional image of a scene, do generate a three-dimensional set of points, e.g., pixels with coordinates or different depth information, which comprise information on surface points of an object. For example, information on a distance of the pixels to the sensor or sensor system itself may be present here. There are some sensors that record not only a two-dimensional image but additionally a depth map, which contains the distances of the individual pixels to the sensor system itself. A three-dimensional point cloud, which represents the recorded scene in 3D, can then also be calculated from this.

Figure 2:
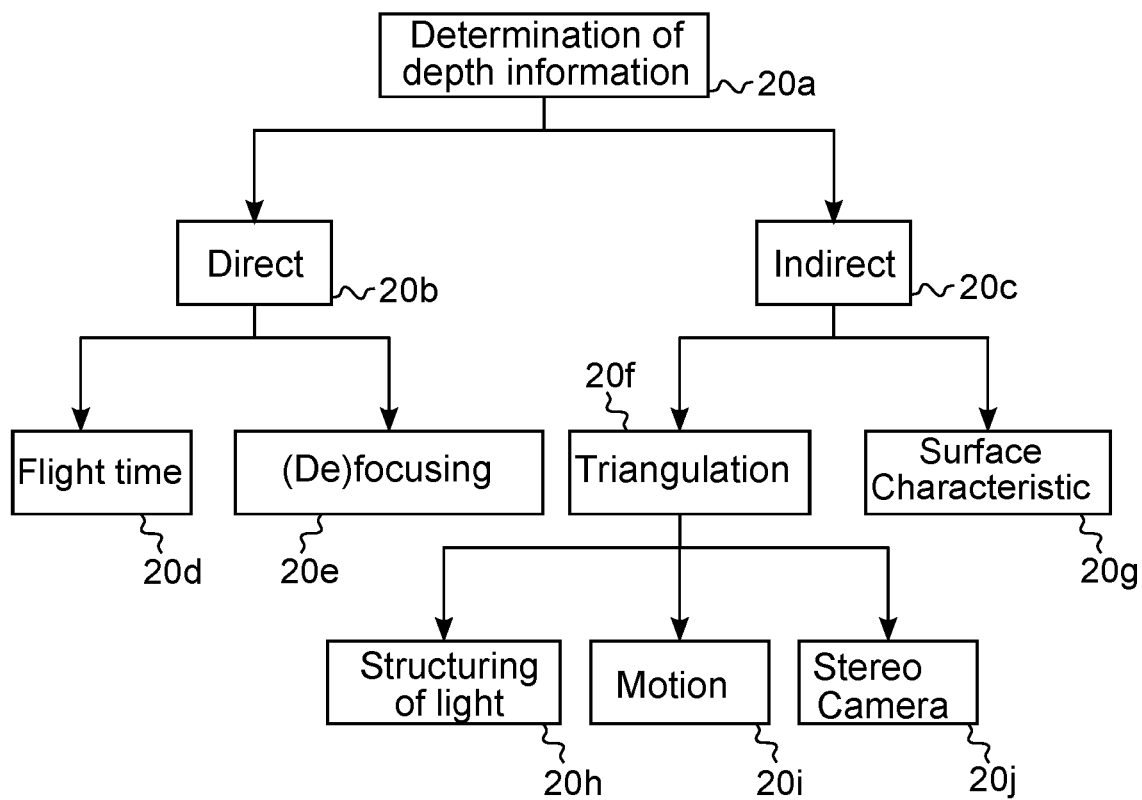
FIG. 2 is an overview diagram of different methods for capturing depth information in exemplary embodiments.

FIG. 2 shows an overview diagram of different methods for capturing depth information in exemplary embodiments. An overview of the different methods for determining the depth information for a depth map is shown in FIG. 2. Distinction can be made between direct methods 20*a*, and indirect methods 20*b*, the distance of a point to the system being determined directly by the system itself with the direct methods and additional methods being needed in the case of the indirect methods. Additional information on the individual possibilities can be found, among other things, in Hartman, 2011. These sensors have become much more favorable and better in the recent past. The three-dimensional information makes it possible for computers to analyze recorded objects more accurately and to derive information of interest, such as distances between objects.

FIG. 2 shows an overview diagram for determining three-dimensional image data in some exemplary embodiments, and variants of determination going beyond FIG. 2 may also be used in exemplary embodiments. It should be pointed out that the three-dimensional image data to which reference is being made here often correspond to a three-dimensional partial image only, because a sensor only determines pixels from a certain perspective and an incomplete three-dimensional image may thus be generated. As will be explained in the further course, a plurality of such partial images may also be combined in order to obtain an image with improved quality or with more pixels, which may, in turn, also correspond only to a partial image.

FIG. 2 shows first in 20*a* the determination or calculation of depth information into image data. Direct methods can now be differentiated in branch 20*b* and indirect methods in branch 20*c*, the former determining the distance of a point to the system via the system directly and the latter requiring additional devices for the determination of the distance. Direct methods are, for example, time of flight measurements 20*d* and (de)focusing methods 20*e*. Indirect methods comprise, for example, triangulation 20*f* (for example, via structured light 20*h*, motion 20*i* or stereo cameras 20*j* and analysis of surface characteristics 20*g*.

Further details of the different possibilities are found, for example, in Hartman F., 2011, see above. Such sensors have become more cost-effective in the past and have been further improved and their performance has been increased. Three-dimensional information can enable a computer to perform corresponding analyses of the captured objects and to provide corresponding data. The three-dimensional information enables computers or computing devices in general to analyze recorded objects more accurately and to derive information of interest, such as distances between objects.

Figure 3:
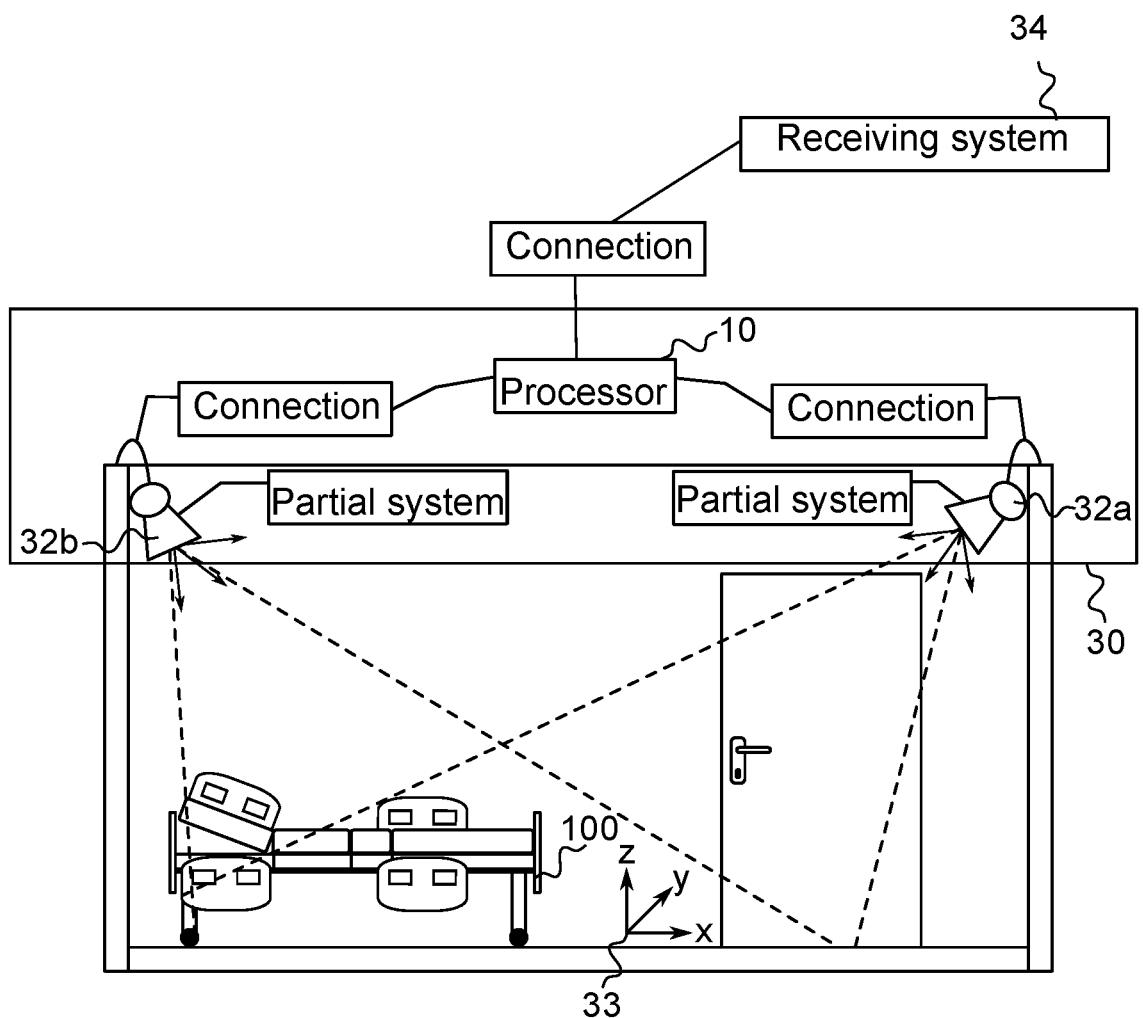
FIG. 3 is a schematic view showing patient surroundings in an exemplary embodiment.

A conceptual representation of a device 30, which is configured to carry out an exemplary embodiment of a method 10, is shown in FIG. 3. FIG. 3 shows patient surroundings, the patient 100 being represented by a hospital bed or patient positioning device. The device 30 comprises here a capturing device with two partial systems or sensors 32*a* and 32*b* for capturing at least three-dimensional partial images from different perspectives of the scene in the hospital room. FIG. 3 shows, moreover, a configurable hospital bed (represented as a general patient positioning device with the patient 100) and a door. The two partial systems 32*a* and 32*b* of the capturing device are coupled via a communication connection, for example, Ethernet and Internet Protocol (IP) and/or in a network, with the determination device/computer, which is implemented here as a processor unit 10 and is configured to execute the above-described method when corresponding software commands are executed thereon. FIG. 3 further shows a Cartesian coordinate system 33, on which the following considerations are based.

The device 30 may generally comprise 1 . . . n sensors, which determine a set of points each, which can be complemented or combined into a single three-dimensional (partial) set of pixels. As the exemplary embodiment in FIG. 3 shows, the capturing device may comprise a plurality of image sensors for detecting at least three-dimensional partial image data. The determination device/computer is then configured to combine the data of the plurality of image sensors into image data of an at least three-dimensional partial image of the patient (here hospital bed) 100. The combined image data contain, for example, information on the three-dimensional surface of the patient positioning device and of the patient 100 from the angles of vision of the sensors 32a, 32b. By combining the data of a plurality of image sensors, a three-dimensional (partial) image of the patient/hospital bed 100 to be imaged can be generated with a higher degree of detail than with a single image.

The computer may be configured in the exemplary embodiment according to FIG. 3 as a processor unit, which is connected to the 1 . . . n sensors via a network. The determination proper may then be carried out based on the combined data. The network, which can provide a communication connection, may also be used to pass on information, for example, for the purposes of documentation, monitoring or display (for example, on a monitor or display screen). FIG. 3 shows a receiving system 34, which may likewise be coupled with the computer via a communication connection, for example, also via a correspondingly configured interface. The receiving system 34 receives information and processes this further, for example, for documentation, safety monitoring, alarm generation, etc.

The view shows two sensors 32a, 32b, which observe the scene and which are connected by a communication connection to the processor unit/computer, which executes the described method 10 and is, in turn, connected itself to receiving systems 34 via a communication connection. The view contains, furthermore, a schematic bed with the patient 100, as it could be used in an intensive care unit. Lateral limitations of the bed are lowered on the side facing the viewer and they are raised on the other side.

The device 30 may accordingly be coupled in exemplary embodiments with 1 . . . n sensors 32a, 32b for capturing the image data. A sensor may yield at least one depth image each (optionally, e.g., also a near infrared image and/or a color image). The sensors may be oriented such that a large part of the patient's bedside 100 to be monitored is located in the field of view. The sensors 32a, 32b are coupled with the processor unit via the communication connections. The result of the method may be transmitted to additional systems, such as alarm or documentation systems, for example, likewise via the communication connection.

Figure 4:
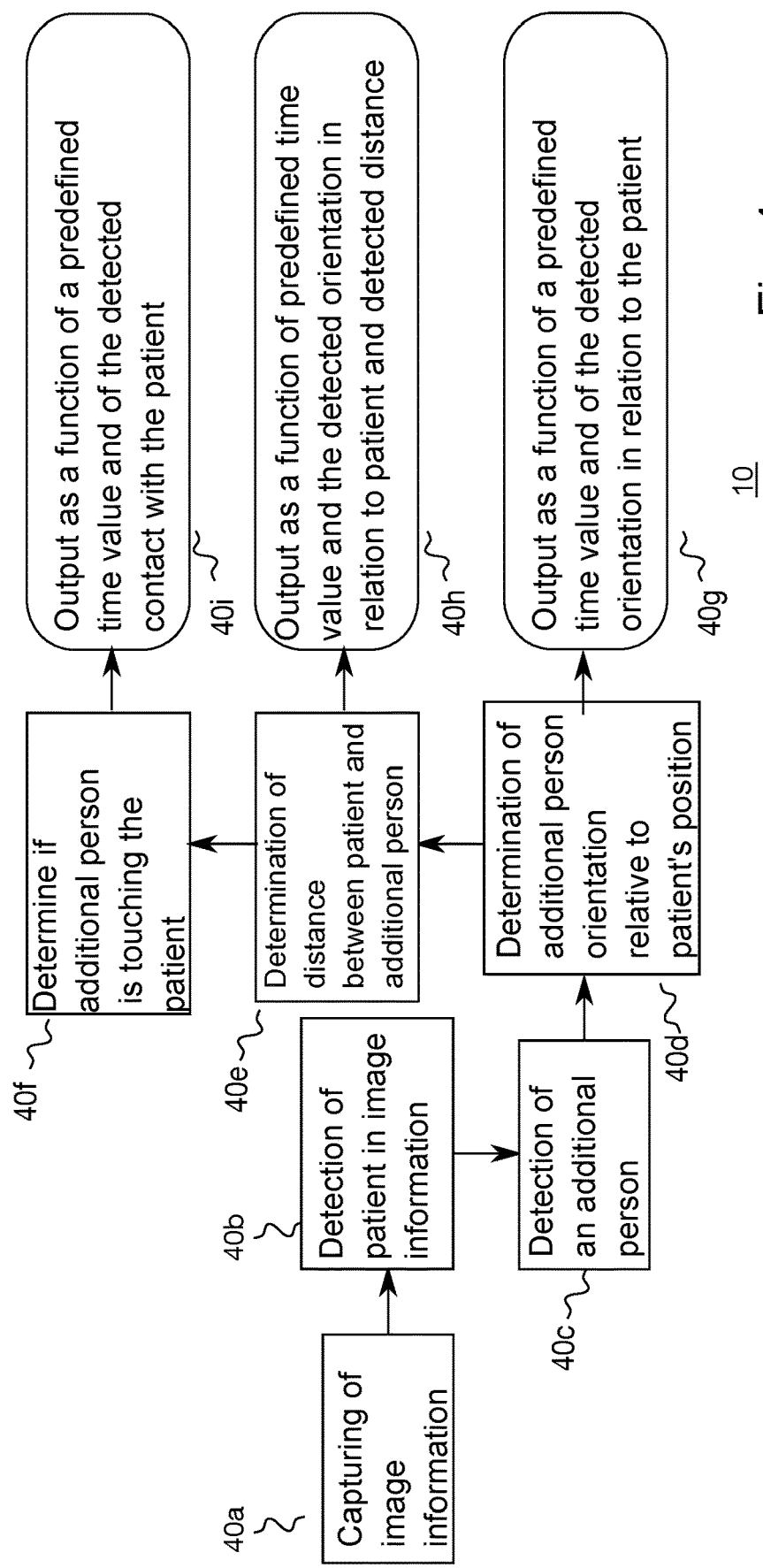
FIG. 4 is a block diagram of another exemplary embodiment of a method for identifying a patient check-up.

FIG. 4 shows a block diagram of another exemplary embodiment of a method 10 for identifying a patient check-up. The method is executed, for example, on the processor unit shown in FIG. 3. The method 10 expects as an input, for example, at least one depth image per available sensor 32a, 32b. This is shown in FIG. 4 by the capture of image information 40a. The patient 100, if he is present in the scene, is automatically detected in the scene by means of this image information or these pieces of image information and his position is determined 40b. Should more than one person be present in the scene, the next part of the method is carried out individually for each patient. A detection of the at least one additional person 40c, for example, of each additional person, who is present in the field of view of the camera, is subsequently performed.

As an alternative, it is possible to take into consideration only persons of certain groups (e.g., only nursing staff members but no visitors). The following rectangular processing blocks 40d, 40e and 40f are carried out now individually for each person thus detected. The respective outputs 40g, 40h, 40i will then also include the results of all detected persons via a predefined time value. If a person is found, the method 10 thus proceeds to determine the orientation of this person, 40d, and to relate this to the previously determined position of the patient. It should be noted that "orientation" may also be replaced with "viewing direction" here. Relating the orientation/viewing direction to the patient's position shall essentially provide an answer to the question of whether or how long the person was oriented towards the patient and/or was looking at him.

If desired, the method may provide at this point an output 40g as a function of a predefined time value and the detected orientation. The method may optionally continue and calculate the distance between the detected person and the detected patient, 40e. The determination 16, cf. FIG. 1, of the geometric relation then comprises a determination of a distance between the at least one additional person and the patient 100. It is then optionally possible to use both the previously determined orientation/viewing direction and the distance determined in 40e to provide, in turn, an output 40h as a function of a time value. In another possible exemplary embodiment, the method 10 can determine whether the person is touching the patient, i.e., whether the patient is being manipulated by the person, 40f. The determination 16, cf. FIG. 1, of the geometric relation then comprises an identification of a contact between the at least one additional person and the patient 100. As a function of this information and of a desired time value, a third output 40i may possibly be provided. It should be noted again that exemplary embodiments of the method 10 do not necessarily have to be able to provide all the outputs that are listed in FIG. 4. Exemplary embodiments may generally comprise an output of information over a time period, during which the geometric relation between the patient 100 and the at least one additional person was present.

If is further possible that additional information is taken into consideration in some exemplary embodiments in the decision on whether or not a warning shall be outputted. This may be, for example, the time of the analysis (day/night), a possibly additionally determined acoustic stress level or the knowledge of performed therapeutic actions (e.g., ventilation maneuvers). The method 10 may accordingly comprise a checking of a time interval for the patient check-up and an output of a warning if identified patient check-ups deviate from the time interval. The time interval may vary, for example, depending on the last nursing action, depending on the daytime/nighttime, depending on patient parameters, etc.

Monitoring for decubitus may, moreover, be carried out in some exemplary embodiments. Possible repositionings of the patient can be identified now, for example, on the basis of a time period, during which a person is present in a defined zone around the patient without interruption, and a comparison with a time value combined with the patient check-up. Moreover, a patient pose may possibly also be identified in exemplary embodiments, for example, with digital image processing means, and a repositioning may thus be identified or validated. However, exemplary embodiments are not fixed to repositionings, but it is also possible to take into consideration general examinations (i.e., generally visual checking as well as physical interactions). Exemplary embodiments may be able to combine a plurality of shorter examinations and to compare these to the predefined time value. Furthermore, an output may also be generated when the time intervals between the examinations are too short to allow the patient to have phases of rest.

Moreover, exemplary embodiments are able to identify, by taking into account the orientation or viewing direction, that a person is leaning with his or her back against the hospital bed, without continuing to view the patient. Incorrect detections of patient check-ups can thus be reduced or possibly even avoided. An incorrect detection is defined here as the detection of a patient check-up, even though no patient check-up has been carried out. In case of an incorrect detection, a nursing staff member could refrain from checking the patient even though this would be identified as such/would be appropriate. Manipulations of the patient can be generally identified in some other exemplary embodiments. In summary, exemplary embodiments can be used extensively and are not specialized to repositionings. General (e.g., visual) check-ups can be identified more reliably by taking into account the orientation/viewing direction and/or manipulations of the patient are identified as such and not only as repositioning of a patient.

The exemplary embodiment described below is based on the procedure explained on the basis of FIG. 1. The sensors used here are 1 . . . n sensors, which generate a depth image each, and, for example, additionally also a near infrared image and/or a color image. Furthermore, it is possible to generate a three-dimensional point cloud from the depth image of each camera. A 2.5 point cloud is also referred to sometimes; this is due to the circumstance that the point cloud does not necessarily image the scene completely due to coverage, and the term "point cloud" includes this possibility as well. If the cameras are calibrated extrinsically, the individual point clouds can also be combined into a global point cloud. The exemplary embodiment being explained here by and large uses only the depth images of the cameras and the point clouds generated therefrom. Additional information may be used in other exemplary embodiments in order to possibly make the method more robust.

Within the framework of this exemplary embodiment, a patient is a person who is located in a patient positioning device (hospital bed, bed of an intensive care unit, etc.) in the scene being viewed. It is therefore sufficient for the purposes of the solution being presented here to detect the patient positioning device (PPD) itself and to decide whether this is being occupied or not. Detecting a PPD in the scene can be accomplished as follows: A fused point cloud of all n sensors is assumed. If these points are projected onto the floor plane (this may be configured either by an authorized person manually, or determined automatically, for example, by means of RANSAC (Fischler, 1981)), a two-dimensional top view of the scene is obtained. Permissible rectangles (i.e., rectangles of a plausible size), which are candidates for PPD, can be detected in this top view. All points within this rectangle up to a predefined level above the floor can be cut out of this point cloud as a validation step to ascertain that the rectangle is, indeed, a PPD. A classifier can then decide whether the cut-out point cloud is a bed or not. There are a number of possibilities of how the classification can specifically look like in the particular case. One possibility would be to generate two-dimensional (2D) projections of the point cloud (e.g., from the top and from the side) and to classify the depth images thus calculated. For example, a Deep Convolutional Neural Network, as it is presented by Krizhevsky, Sutskever, and Hinton, 2012, would be suitable for this.

As an alternative, the classification may also be carried out directly on the basis of the point cloud. Song and Xiao, 2014, describe how features that can be classified with SVMs (Support Vector Machine in English) can be obtained from the point cloud. If a PPD is identified in the scene, the method proceeds to determine whether this is occupied or not. A possibility for this is explained in the publication by Martinez, Schauerte and Stiefelhagen, 2013. A Bed Aligned Map (approximately a vector map aligned at the bed) is used there as a feature vector in order to solve the occupation of a PPD as a classification problem.

The position of the patient, which will still be needed in the course of the method, can easily be determined approximatively, because the extracted point cloud is present. The center of this partial point cloud is a sufficient approximation for the center of gravity of the patient. For further details concerning PPDs and also concerning the further aspects explained here, reference is made to the document DE 10 2015 013 031.5, which pertains to the determination of partial segment layers of a PPD 100 based on image data.

Figure 5:
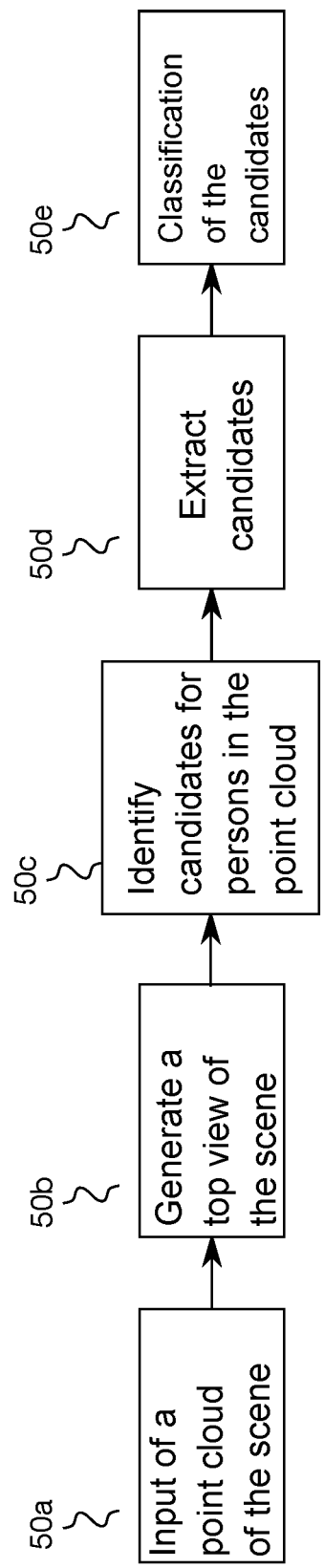
FIG. 5 is a block diagram of another exemplary embodiment of a method for identifying additional persons.

As was already described above, at least one additional person is also detected in exemplary embodiments next to the patient in the scene. It may be important in this connection to possibly identify all persons. The method may also be configured in some exemplary embodiments for possibly detecting and counting only persons of certain groups of persons as such. One possibility of detecting persons in the scene is shown schematically in FIG. 5. FIG. 5 illustrates a block diagram of another exemplary embodiment of a method for identifying additional persons. The method operates with a point cloud as a representation of the scene, which is captured and inputted as described above, 50a. The method proceeds by generating at first a top view of the 50b, and by identifying candidates for persons in this top view, 50c. Unlike in the above description, connected pixels ("blobs"), which could describe a person from the top, rather than rectangles are searched for in this exemplary embodiment. The blobs are examined for this on the basis of different parameters, such as their height, circularity and convexity. Among other things, the "SimpleBlobDetector" from the OpenCV library may be used for this.

It should be noted that a detected motion can be used in some exemplary embodiments when generating the top view of the scene to rule out static objects as candidates. A possible "tracker" (see below) must now ensure that a person is not considered to have disappeared as soon as she remains motionless over a certain time. If the candidates are identified, these are, in turn, extracted from the point cloud, 50d, in order to make it possible later to classify them, 50e. The classification can then be carried out in exactly the same manner as above, and the classifiers may, of course, be trained here correspondingly for identifying the person. It may be desirable in some exemplary embodiments to identify only persons from certain groups of persons as such. In particular, it may be appropriate to identify only nursing staff members as persons.

Possibilities of achieving this would be: If color images are available, these may help identity groups of persons, because nursing staff members wear special work clothes especially in hospitals. The method could be configured such that it identifies only persons who appear wearing clothes in the color of the work clothes as such. For example, color images of nursing staff members would have to be made available to the system for this. One or more color histograms can be calculated from this, and these can then be used additionally for the classification of the candidates. The drawback of this possibility is that it is only available in case of sufficient light conditions. In some other exemplary embodiments, the method may comprise an identification of whether the at least one additional person is a nursing staff member as well as an identification of the patient check-up based on the at least one geometric relation if the person is a nursing staff member. In other words, at least some exemplary embodiments may require the performance of the patient check-up by a nursing staff member.

The identification of whether the at least one additional person is a nursing staff member may be based here on a color analysis of pixels of the at least one additional person in the image data. For example, a color detection of the clothing of the at least one additional person may be carried out. The identification of the nursing staff member may be based in further exemplary embodiments on an identifier of the nursing staff member. Optical identifiers, face recognition, marking, bar codes, acoustic identifier, for example, ultrasound, transponders, e.g., Radio Frequency IDentification (RFID), pager/smartphone tracking, etc., are conceivable in this connection. The method may comprise, moreover, a determination of a plurality of additional persons in the patient surroundings. Thus, at least some exemplary embodiments can also distinguish persons or groups of persons. For example, visitors, physicians, nurses, etc. The system may be able to be configured correspondingly here (the variety of distinction does not have to be the same for all patients). For example, a plurality of methods may be operated simultaneously in order to identify persons of the different groups of persons.

Sitting persons can be excluded in some exemplary embodiments in order to reduce the influence of visitors. This may likewise be integrated in the classification step by a classifier being trained especially for sitting persons. Identification via RFID characteristics or the like would be possible as well. As was described above, the position of each person can be approximated as the center of the respective extracted point cloud here as well. Further, it is possibly meaningful to track a person over several frames— the so-called "tracking." Persons may also be tracked through a room by means of tracking algorithms.

If the persons in the individual frames are identified, these are associated with one another over frames in a step called "Data Association." It can be decided by means of cost functions whether a detected person belongs to a person from the last frames or not. Examples of such cost functions are the distance of the individual detections to one another (or a "Bounding-Box Overlap") or the comparison of the texture of the persons in the near infrared and/or color image. If a person was tracked over a plurality of frames, it is also possible to predict future positions, e.g., by means of a Kalman filter (Welch and Bishop). The predicted position can then be compared with the positions of the detections. It should further be pointed out that, among other things, the Software Development Kit (SDK) for the Kinect camera of Microsoft provides functions with which persons can be detected and tracked.

As was mentioned already, exemplary embodiments carry out a determination of the orientation or of the viewing direction of the additional person in relation to the patient's position. Both the orientation of the person and the (more exact) viewing direction of the person may be used. It should be explained here for both procedures how these can be implemented as an example. If the persons are being tracked ("tracking"), a simple approximation for the orientation of a person is the latter's most recent walking direction, which can then easily be determined over the sequence of different positions of the person in the last frames. A method such as that explained in Lallemand, Ronge, Szczot and Ilic, 2014, in which the orientation of a person is considered to be a classification problem, which is solved by means of HOG features (from the English Histograms of Oriented Gradients), cf. Dalal and Triggs, 2005, and Random Forests, cf. Breiman, 2001, would be more precise. The Kinect-SDK already mentioned before can also be used to determine an orientation, because the full body pose is outputted as well.

A possibility to approximate the viewing direction is to determine the orientation of the head. Previous studies, which can be used, are already available for this purpose as well. Depth images and Random Regression Forests are used in Fanelli, Weise, Gall and Van Gool, 2011, to determine the orientation of the head. Rehder, Kloeden and Stiller, 2014, use a part-based classifier to identify the head of a person, and the orientation of the head is solved, in turn, as a classification problem for LBP (English Local Binary Pattern) features. It would also be possible to use eye trackers to further optimize the determined viewing direction. Determination of the distance between the patient and the additional person is carried out in some exemplary embodiments. A relatively accurate calculation of the distance between objects is possible with the use of depth cameras. It was already explained above how the positions of the patient and of the detected persons can be determined. If these positions are given, a determination of the distance of the patient P to the person Q is a calculation of the distance between two points in the three-dimensional space.

Figure 6:
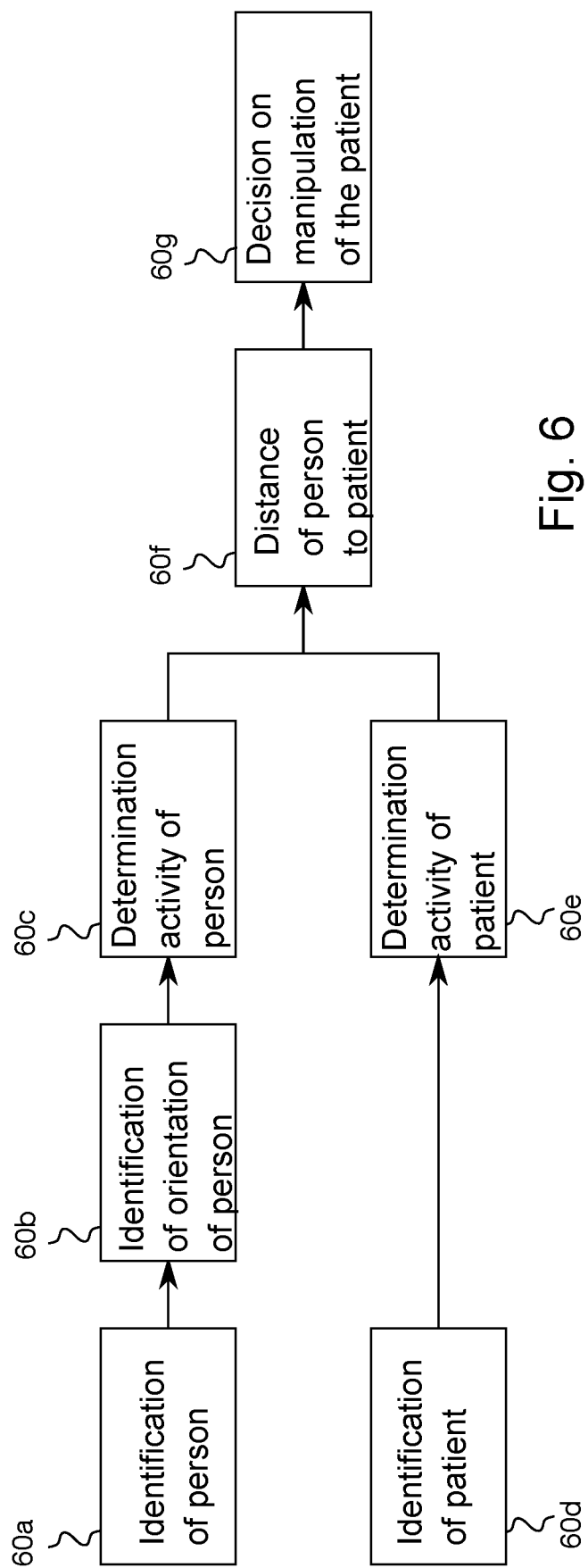
FIG. 6 is a block diagram of another exemplary embodiment of a method for identifying a patient manipulation.

As a last step, the method is aimed at identifying manipulations at the patient, for example, by detecting whether a contact is taking place between the patient and an additional person. This is manifested by motion/activity of the patient or directly at the patient, which is not induced by the patient himself. "Passive activity/motion" will also be referred to below. A technical solution to identifying a manipulation of the patient is shown schematically in FIG. 6. FIG. 6 shows a block diagram of another exemplary embodiment of a method for identifying a manipulation of the patient.

It is assumed in this connection that a decision is made individually for each <person, patient> pair of a person and patient whether a manipulation takes place or not. The method thus begins with the identification of the person, 60a, with the orientation thereof, 60b, and the patient, 60d. Possible implementations were already explained above in this connection. The activity of the person, 60c, can be quantified in the same manner as for the patient, 60e. Either the particular extracted partial point cloud or the partial detail corresponding to this in the depth, color or near infrared image can be considered for this purpose. Exemplary embodiments that are based on the partial point cloud may use, for example, methods that are described in Girardeau-Montaut et al., 2005. A corresponding example is also contained in the Point Cloud Library. The possibility of solving the problem on the basis of one of the above-mentioned two-dimensional images shall be discussed in more detail here.

The corresponding partial image may be determined for different times (for example, every 0.1 second), so that a sequence of partial images that is meaningful in time develops. The motion or activity of the patient or person can then be quantified by the analysis of the changes in the partial images over time. The analysis of the changes in the n partial images, which shall be designated by $t_1 \ldots t_n$ in their sequence over time, may be carried out in different manners. Possibilities for this are:

1. Absolute differential image:
   Calculate for each pair $t_i \ldots t_{i-1}$ the absolute difference of the pixel values for each pixel position, resulting in image D.
   Compare the individual differences with a threshold value s1 and write $$V(x, y) = \begin{cases} 0, & \text{if } D(x, y) < s1 \\ 1, & \text{IF } d(X, Y) \geq s1 \end{cases}.$$

The sum of the pixels in V with the value 1 is now an indicator of the activity at the time i.

2. Motion History Image (MHI):

MHIs function similarly to the absolute differential image, but they also take into account changes at the time i that occurred more than a step ago. In a certain way, an MHI is therefore a weighted combination of a plurality of background images V from Example 1 and the sum of the pixel values of the MHIs can be used as a quantification of a longer-lasting motion. MHIs are explained in more detail in the following article: Ahad, Tan, Kim, and Ishikawa, 2012.

3. Sample-based background subtraction:

Depending on the selection of the needed threshold values in 1 and 2, the corresponding indicators may be susceptible to noise or are not sensitive enough to true motion. There are therefore methods that take the history of a pixel into consideration in more detail in order to decide whether or not this pixel represents activity. A known and successful example of this is ViBe: Barnich and Van Droogenbroeck, 2011. ViBe generates, in turn, an activity map, in which a pixel receives the value 1 if it experiences activity and the value 0 if this is not the case. Therefore, the sum of the pixel values is also an indicator of the activity.

The characteristics for activity may, moreover, also be normalized by the sums being divided by the number of pixels of the partial image being considered. The above-described methods yield a sequence of characteristics $k_1 \ldots k_m$ describing the activity, which is meaningful over time (time series). Furthermore, in order to improve the method, it is also possible to further limit the partial images being considered, especially that for the patient. Since it is known how the person and the patient are located in relation to one another in the room, it would be possible to modify the partial images such that only the side of the image facing the respective other object is taken into consideration.

The distance of the person to the patient can, furthermore, be determined analogously to the above description. The method now decides on the basis of the information collected up to now whether a manipulation of the patient is taking place or not. The method now decides in this exemplary embodiment in favor of the presence of a manipulation during a time period T if the following points are given during the time T:

a) A person (P) is located in the immediate vicinity of the patient (i.e., the distance measurement yielded a value<X), b) (P) is oriented in the direction of the patient positioning device, and c) Sufficient activity (i.e., the determined characteristics of the activity exceed a threshold value S several times during the time period T) is detected both at (P) and at (Pat).

Figure 7:
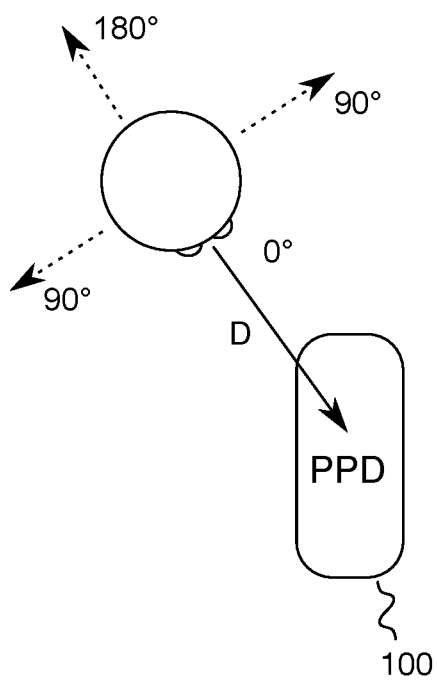
FIG. 7 is an illustration for determining orientation and distance between a patient and an additional person in an exemplary embodiment.

Possible essential components, which are used to determine/identify a patient check-up in exemplary embodiments, were explained in the above subsections. The output, which the method shall yield in some further exemplary embodiments, will then depend by and large on the intended use of the method and the application thereof. Another application example, in which the captured information is used to help guarantee appropriate intervals between patient check-ups or manipulations, should be explained here. These intervals may be either too long, which results in gaps in the checking, or too short, as a result of which hardly any phases of rest may possibly be allowed for the patient. FIG. 7 shows an illustration for determining the orientation and the distance D between a patient and an additional person in an exemplary embodiment. FIG. 7 shows a PPD 100 and a nursing staff member, whose relative orientation in relation to one another is in a (value) range between 0° and 180°. FIG. 7 shows the angle ratios from the view of the nursing staff member. If the PPD 100 is in the range around 0° during a certain time, a patient check-up may be assumed.

In some additional exemplary embodiments, both the determined orientation O(t) and the distance D(t) (FIG. 7 is used for the illustration) as well as the analysis of whether the patient is manipulated, M(t)) are included in an output. These variables are always analyzed at a certain time t. It should be pointed out that there also may be other exemplary embodiments that do not use all these pieces of information. According to the flow chart in FIG. 8, O(t), D(t) and M(t) are included in the calculation of a number of points P(T) according to the following formula:

$$P(T) = \sum_{persons} \int_{t=L}^{T} f(t) \cdot (k_1 \max(0.90 - O(t)) \cdot k_2 \max(0.5 - D(t)) + k_3 M(t)).$$

Here, t runs over time from the time L last selected in the past to the current time T. The $k_i$, i=1, 2, 3, are factors that can be used individually to weight O(t), D(t) and M(t). The term f(t) is a function that calculates a weighting as a function of the time of day. It would thus be possible to calculate, for example, that less checking is necessary during the night. Accordingly, checking of the time interval may comprise in method 10 in exemplary embodiments an analysis of a time of day-dependent function together with one or more weighted geometric relations.

Thus, P(T) is a number of points that increases with increasing duration and intensity with which detected persons have attended to the patient since the last time L. P may now be compared with a threshold value S as follows:

If P(T)>S, add T in the time series Z and write L=T. The time series Z can now be analyzed by comparing this, for example, with a time value ZW. If all time stamps in Z occurred more than ZW ago, the checking of the patient should be increased. If Z contains very many time stamps that occurred not more than ZW ago, the checking and other actions disturbing rest should be reduced. This information can now be transmitted as a warning, for example, to the nursing staff. The time value ZW may also be varied in some exemplary embodiments depending on the time of day, with which it would be possible to control the frequency at which the checks should take place. The addition of T to the time series Z can be considered as the resetting of a counter. If the counter reaches a value greater than ZW, the checking should be increased. The checking should be reduced if the counter is reset too often during the time interval ZW.

Figure 8:
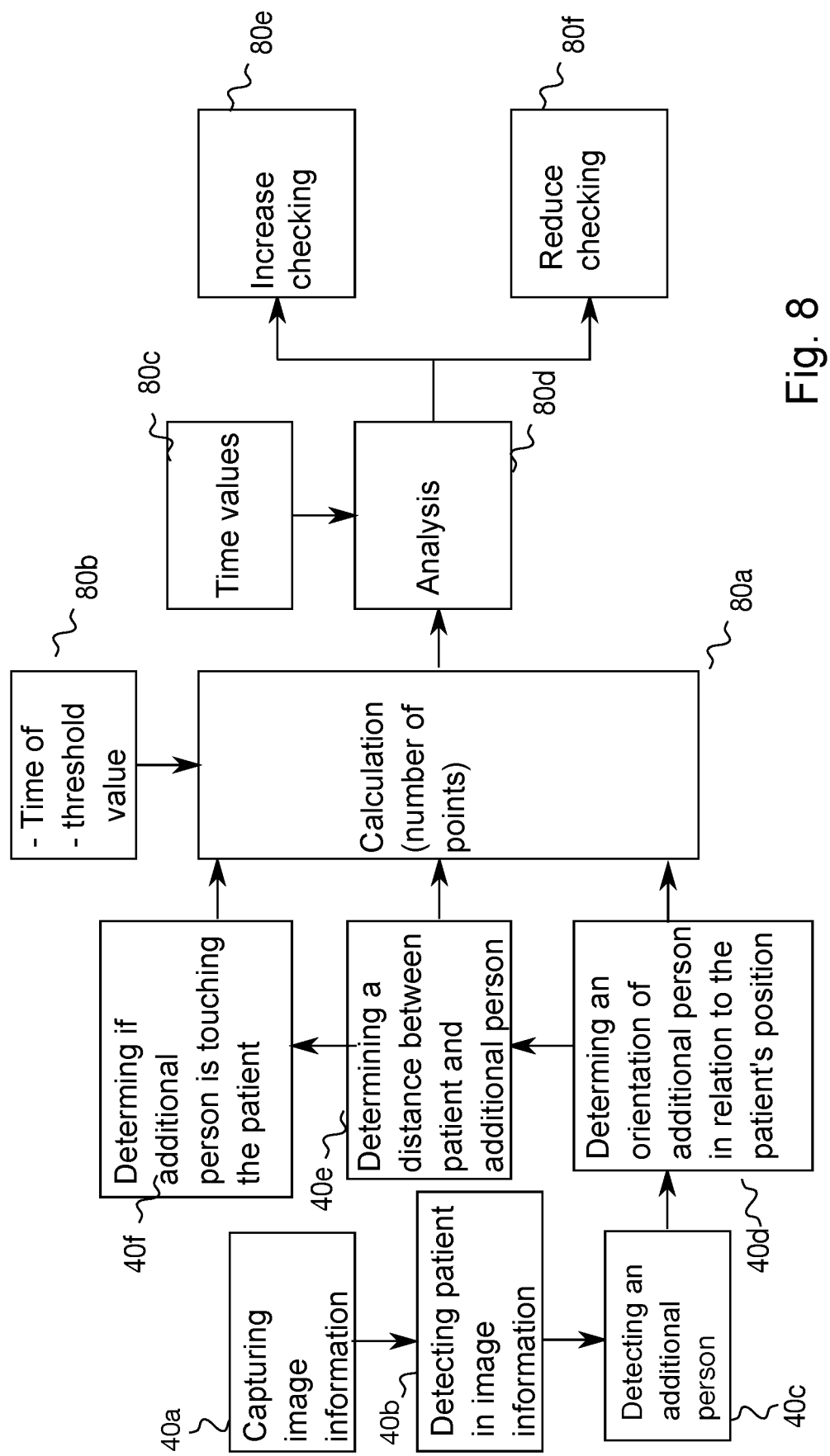
FIG. 8 is a block diagram of another exemplary embodiment of a method for determining whether a patient checking should be increased or reduced in an exemplary embodiment.

FIG. 8 shows a block diagram of another exemplary embodiment of a method for determining whether a patient checking should be increased or reduced in an exemplary embodiment. FIG. 8 shows the same steps as FIG. 4, the only difference being that the outputs are now effected into a calculation of the number of points 80a, in which the time and a threshold value 80b are also included. The number of points can subsequently be analyzed, 80d. Based on the analysis, an increase 80e or a reduction of the intervals between checkings, 80f, can then be carried out. In this exemplary embodiment, the method 10 comprises a determination of information on whether the patient should be checked up more frequently or less frequently, and an outputting of this information. In further exemplary embodiments, the method 10 may further comprise a documentation of identified patient check-ups, for example, also video data in exceptional cases. For example, suggestions on documentation may be made for a nursing staff member based on the method 10, and these suggestions may then be taken into consideration by the nursing staff member.

A care device can make it credible by means of the documentation that the care for its patient was sufficient. A documentation may be useful in future work shift scheduling. It may be possible, for example, to identify time periods during which patients are cared for systematically too infrequently or too often. It would be possible to evaluate with a comparison of the documentation with the visiting times whether a patient is possibly prevented by visitors from having sufficient rest. In some other exemplary embodiments, the method may be carried out upon receipt of alarm information from a medical device. Such alarm information may be triggered, for example, by a patient monitor when a captured parameter is identified as being critical. It can now be monitored whether a patient check-up was carried out within a predefined time period upon receipt of the alarm information. The patient check-up associated with the alarm or resulting from the alarm can then be identified with an exemplary embodiment of the method. Exemplary embodiments can thus provide possibilities for analyzing, for example, a relation over time between an alarm and a corresponding patient check-up. The documentation can be compared in some exemplary embodiments with other information, e.g., the heart rate of a patient, e.g., in order to determine whether and to what extent and in what form a patient is stressed or calmed down by the presence of a person.

In further exemplary embodiments, the method may be started by an alarm. Alarms, which are provided by a medical device, for example, an alarm that the heart rate of the patient exceeds an upper threshold value, are examples of this. The method can then start with the identification of patient check-ups and then trigger an output. Examples of this output could be that the system sends an "alarm off" command to the medical device originally generating the alarm (for example, when a patient check-up was detected). It would also be possible that the system itself triggers another alarm, which may possibly have different recipients than the original alarm (e.g., when a certain time period has passed after the original alarm). Furthermore, a documentation of the identified patient check-ups is possible here as well.

The patient safety can be increased in some exemplary embodiments insofar as it can later be established with a high probability whether a person was present in the vicinity of the patient during a certain time period. It is thus possible at least in some exemplary embodiments, e.g., to establish whether the person was possibly disturbed willfully or whether there was a failure to offer assistance. The method may also be used in exemplary embodiments to document the presence (including additional information, such as the orientation, the distance and whether manipulation of the patient took place) of persons at the patient. These pieces of information can be used in different manners. One possibility would be to bring the documentation data into connection with predefined data. These predefined data could indicate legal, work-scheduling or organizational requirements. For example, the predefined data could contain data on the time intervals at which a patient should be seen. The predefined data could also offer information on how rapidly a patient check-up should take place after a certain event. A comparison of these predefined data with the documentation data makes it consequently possible to check the compliance with these specifications.

It is, furthermore, possible to analyze the documentation data to determine when patient check-ups have taken place and whether these happened especially frequently or especially infrequently during certain time intervals. This can also be associated with predefined data, which indicate, for example, the number of check-ups that should be favored for a duration, when visitation times are or how the work schedule of the nursing staff members looks like. It would be possible, for example, to infer from these comparisons whether or when a sufficient number of nursing staff members are on duty and when not (which could affect the work schedule). The results of the comparisons of the documentation data with the predefined data can subsequently be made available or outputted (for a user).

Figure 9:
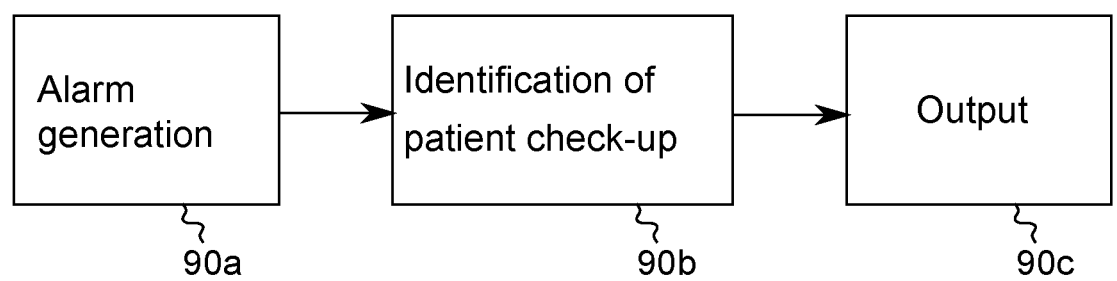
FIG. 9 is a block diagram of another exemplary embodiment of a method for identifying a patient check-up following an alarm generation.

FIG. 9 shows a block diagram of another exemplary embodiment of a method for identifying a patient check-up after an alarm generation. The alarm generation takes place in a step 90a and the above-described method for identifying a patient check-up subsequently takes place in step 90b. Based on the check-up from step 90b, an output can then be effected in step 90c. The above-described method can be started by an alarm in such an exemplary embodiment. Examples of this are alarms that are provided by a medical device, for example, an alarm indicating that the heart rate of the patient exceeds an upper threshold value. The method can then begin with the identification of patient check-ups and subsequently trigger an output. Examples of this output could be that the system sends an "alarm off" command to the medical device originally triggering the alarm (e.g., when a patient check-up was detected). It would also be possible that the system itself triggers another alarm, which may possibly have different recipients than the original alarm (e.g., when a certain time period has passed after the original alarm). Furthermore, documentation of the identified patient check-up is possible here as well.

Figure 10:
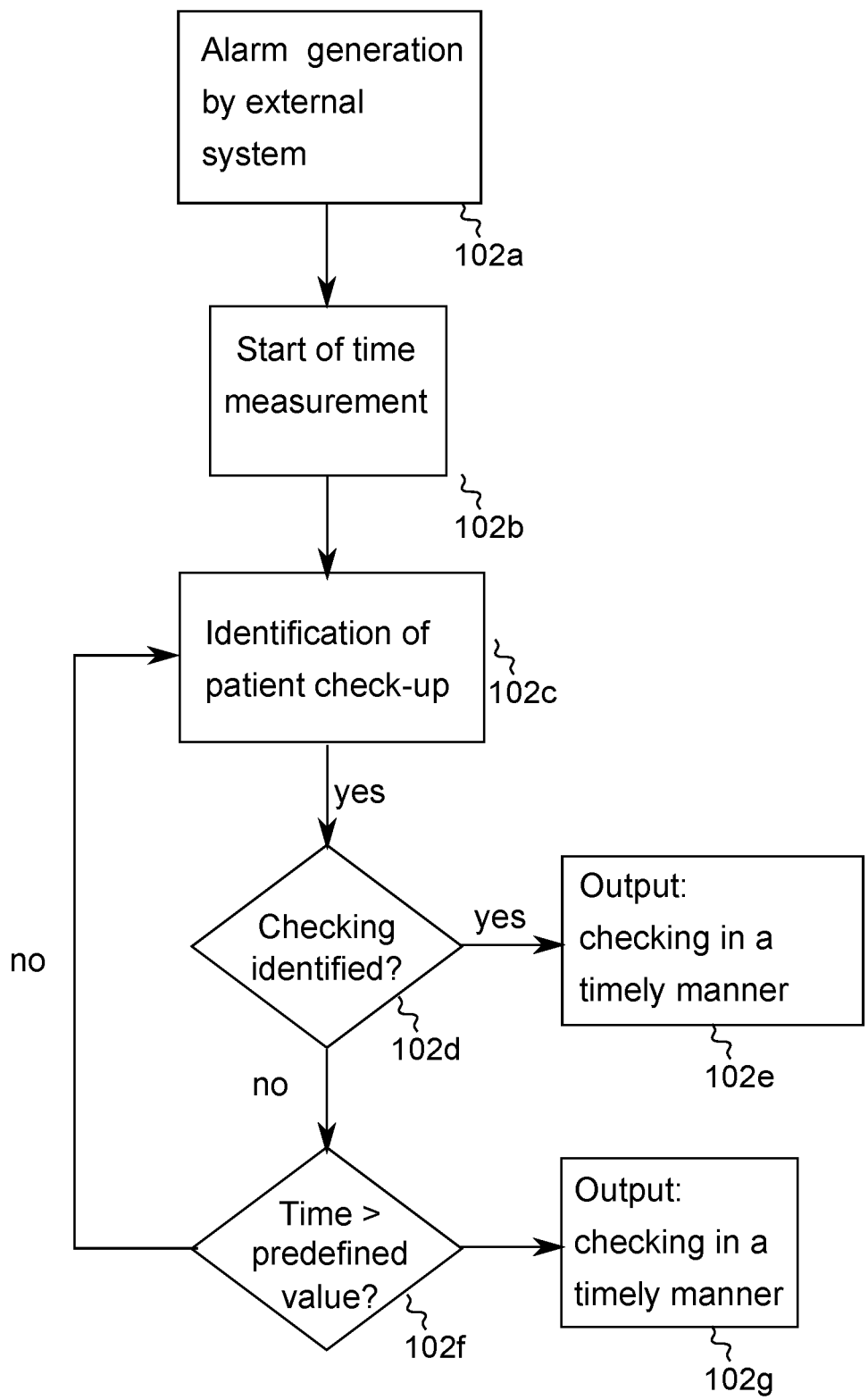
FIG. 10 is a block diagram of another exemplary embodiment of a method for identifying a patient check-up following an alarm generation by an external system.

FIG. 10 shows a block diagram of another exemplary embodiment of a method for identifying a patient check-up after an alarm generation by an external system. The external system may be, for example, a patient monitor. An alarm generation is carried out by the external system in step 102a, whereupon a time measurement is started in step 102b. The already described method for identifying a patient check-up is started in step 102c. If a check-up is then identified in step 102d, an output, which indicates that the check-up was performed in a timely manner, can take place in step 102e. If the measured time exceeds a predefined value (polling in step 102f), an output indicating that the check-up did not take place in a timely manner is carried out in step 102g. The exemplary embodiment implements a method that decides whether a patient check-up was carried out in a timely manner as a response to an alarm of the external system.

The features disclosed in the above description, in the claims and in the drawings may be significant both individually and in any desired combination for the embodiment of exemplary embodiments in the different configurations thereof and, unless the description shows something different, they may be combined with one another as described.

Even though some aspects were described in connection with a method or with a device, it is obvious that these aspects also represent a description of the corresponding device or of the corresponding method, so that a block or a component of a device can also be defined as a corresponding method step or as a feature of a method step and vice versa. Analogously to this, aspects that were described in connection with or as a method step also represent a description of a corresponding block or detail or feature of a corresponding device.

Depending on certain implementation requirements, exemplary embodiments of the present invention may be implemented in hardware or in software. The implementation may be carried out with the use of a digital storage medium, for example, a floppy disk, a DVD, a Blu-Ray disk, a CD, a ROM, a PROM, an EPROM, an EEPROM or a FLASH memory, a hard drive or another magnetic or optical memory, on which electrically readable control signals are stored, which can or do interact with a programmable hardware component such that the method in question will be executed.

A programmable hardware component may be formed by a processor, a computer processor (CPU=Central Processing Unit), a graphics processor (GPU=Graphics Processing Unit), a computer, a computer system, an application-specific integrated circuit (ASIC), an integrated circuit (IC), a system on chip (SOC), a programmable logic element or a field-programmable gate array with a microprocessor (FPGA).

The digital storage medium may therefore be machine- or computer-readable. Some exemplary embodiments consequently comprise a data storage medium, which has electronically readable control signals, which are capable of interacting with a programmable computer system or with a programmable hardware component such that one of the methods described here will be executed. An exemplary embodiment is thus a data storage medium (or a digital storage medium or a computer-readable medium), on which the program for executing one of the methods described here is recorded.

Exemplary embodiments of the present invention may generally be implemented as a program, firmware, computer program or computer program product with a program code or as data, wherein the program code or the data act such as to execute one of the methods when the program is running on a processor or on a programmable hardware component. The program code or the data may also be stored, for example, on a machine-readable medium or data storage medium. The program code or the data may be present, among other things, as source code, machine code or byte code as well as as other intermediate code.

Another exemplary embodiment is, further, a data stream, a signal sequence or a sequence of signals, which data stream or sequence represents or represent the program for executing one of the methods being described here. The data stream, the signal sequence or the sequence of signals may be configured, for example, such as to be transferred via a data communication connection, for example, via the Internet or another network. Exemplary embodiments are consequently also signal sequences representing data, which are suitable for a transmission via a network or a data communication connection, wherein the data represent the program.

A program according to an exemplary embodiment may implement one of the methods during its execution, for example, by this reading storage locations or by writing a datum or a plurality of data into these, whereby switching operations or other processes are possibly elicited in transistor structures, in amplifier structures or in other electrical, optical, magnetic components or in components operating according to another principle of function.

Data, values, sensor values or other pieces of information may correspondingly be captured, determined or measured by a program by reading a storage location. A program may therefore capture, determine or measure variables, values, measured variables and other pieces of information by reading one or more storage locations as well as bring about, prompt or execute an action as well as actuate other devices, machines and components by writing into one or more storage locations.

The above-described exemplary embodiments represent merely an illustration of the principles of the present invention. It is obvious that modifications and variations of the arrangements and details being described here may be clear to other persons killed in the art. It is therefore intended that the present invention be limited only by the scope of protection of the following patent claims rather than by the specific details, which were presented here on the basis of the description and the explanation of the exemplary embodiments.

While specific embodiments of the invention have been shown and described in detail to illustrate the application of the principles of the invention, it will be understood that the invention may be embodied otherwise without departing from such principles.

The invention claimed is:

1. A method for capturing optical image data of patient surroundings and for identifying a patient check-up based on the image data, the method comprising the steps of:
   receiving captured optical image data of patient surroundings;
   detecting a patient based on the optical image data;
   detecting at least one additional person based on the optical image data;
   determining at least one geometric relation between the patient and the at least one additional person based on the optical image data, wherein determining the geometric relation comprises determining a body orientation of the at least one additional person in relation to the patient, and/or determining a viewing direction by an orientation of the head or eyes of the at least one additional person in relation to the patient based on the optical image data; and
   identifying the patient check-up based on the geometric relation and on a time period during which the geometric relation between the patient and the at least one additional person was present.

2. A method in accordance with claim 1, wherein determining the geometric relation comprises determining a distance between the at least one additional person and the patient based on the optical image data.

3. A method in accordance with claim 1, wherein determining the geometric relation comprises identifying contact between the at least one additional person and the patient based on the optical image data.

4. A method in accordance with claim 1, further comprising outputting information over the time period, during which the geometric relation between the patient and the at least one additional person was present.

5. A method in accordance with claim 1, further comprising checking a time interval for the patient check-up and outputting a warning if identified patient check-ups deviate from the time interval.

6. A method in accordance with claim 5, wherein checking the time interval comprises analyzing a time of day-dependent function together with one or more weighted geometric relations.

7. A method in accordance with claim 1, further comprising identifying whether the at least one additional person is a nursing staff member and identifying the patient check-up based on the at least one geometric relation if the person is a nursing staff member.

8. A method in accordance with claim 7, wherein identifying whether the at least one additional person is a nursing staff member is based on a color analysis of pixels of the at least one additional person in the optical image data.

9. A method in accordance with claim 7, identifying the nursing staff member is based on an identifier of the nursing staff member.

10. A method in accordance with claim 1, further comprising detecting a plurality of additional persons in the patient surroundings based on the optical image data.

11. A method in accordance with claim 1, further comprising executing a process after receiving alarm information from a medical device.

12. A method in accordance with claim 11, further comprising monitoring to determine whether a patient check-up is carried out within a predefined time period after receipt of the alarm information.

13. A method in accordance with claim 1, further comprising determining a piece of information on whether the patient should be checked up more frequently or less frequently and an outputting of this information.

14. A method in accordance with claim 1, further comprising documenting identified patient check-ups.

15. A device comprising: a computer, a processor or a programmable hardware component, which computer, processor or programmable hardware component is configured to execute a method comprising the steps of:
   receiving captured optical image data of patient surroundings;
   detecting a patient based on the optical image data;
   detecting at least one additional person based on the optical image data;
   determining at least one geometric relation between the patient and the at least one additional person, wherein determining the geometric relation comprises determining a body orientation, and/or determining a viewing direction by an orientation of the head or eyes of the at least one additional person in relation to the patient based on the optical image data; and
   identifying the patient check-up based on the determined geometric relation and on a time period during which the geometric relation between the patient and the at least one additional person was present.

16. A method according to claim 1, wherein program code is used for executing at least one of the method steps on the computer, on the processor or on the programmable hardware component.

17. A device in accordance with claim 15, wherein determining the geometric relation comprises at least one of:
   determining a distance between the at least one additional person and the patient based on the optical image data; and
   identifying contact between the at least one additional person and the patient based on the optical image data.

18. A device in accordance with claim 17, further comprising outputting information over a time period, during which the geometric relation between the patient and the at least one additional person was present.

19. A device in accordance with claim 15, further comprising checking a time interval for the patient check-up and outputting a warning if identified patient check-ups deviate from the time interval.

20. A device in accordance with claim 15, further comprising identifying whether the at least one additional person is a nursing staff member and identifying the patient check-up based on the at least one geometric relation if the person is a nursing staff member.

21. A method for capturing optical image data of patient surroundings and for identifying a patient check-up based on the image data, the method comprising the steps of:
   receiving captured optical image data of patient surroundings;
   detecting a patient based on the optical image data;
   detecting at least one additional person based on the optical image data;
   determining at least one geometric relation between the patient and the at least one additional person based on the optical image data, wherein determining the geometric relation comprises determining a body orientation of the at least one additional person in relation to the patient, and/or determining a viewing direction by an orientation of the head or eyes of the at least one additional person in relation to the patient based on the optical image data, and identifying contact between the at least one additional person and the patient based on the optical image data;
   identifying the patient check-up based on the geometric relation;
   outputting information over a time period, during which the geometric relation between the patient and the at least one additional person was present; and
   checking a time interval for the patient check-up and outputting a warning if identified patient check-ups deviate from the time interval, and wherein checking the time interval comprises analyzing a time of day-dependent function together with one or more weighted geometric relations.

\* \* \* \* \*